(12) United States Patent
Hong et al.

(10) Patent No.: US 11,534,399 B2
(45) Date of Patent: Dec. 27, 2022

(54) INHALABLE LIPOSOMAL SUSTAINED RELEASE COMPOSITION FOR USE IN TREATING PULMONARY DISEASES

(71) Applicants: Taiwan Liposome Co., Ltd., Taipei (TW); TLC Biopharmaceuticals, Inc., South San Francisco, CA (US)

(72) Inventors: Keelung Hong, South San Francisco, CA (US); Jonathan Fang, South San Francisco, CA (US); Yu-Cheng Tseng, Taipei (TW); Ting-Yu Cheng, Taipei (TW); Wan-Ni Yu, Taipei (TW); Jo-Hsin Tang, Taipei (TW)

(73) Assignee: INSPIRMED CORP., Taipei (TW)

( * ) Notice: Subject to any disclaimer, the term of this patent is extended or adjusted under 35 U.S.C. 154(b) by 0 days.

(21) Appl. No.: 17/045,940

(22) PCT Filed: Apr. 23, 2019

(86) PCT No.: PCT/US2019/028647
§ 371 (c)(1),
(2) Date: Oct. 7, 2020

(87) PCT Pub. No.: WO2019/209787
PCT Pub. Date: Oct. 31, 2019

(65) Prior Publication Data
US 2021/0145740 A1    May 20, 2021

Related U.S. Application Data

(60) Provisional application No. 62/661,217, filed on Apr. 23, 2018.

(51) Int. Cl.
*A61K 9/00* (2006.01)
*A61K 9/127* (2006.01)
(Continued)

(52) U.S. Cl.
CPC .......... *A61K 9/0078* (2013.01); *A61K 9/1272* (2013.01); *A61K 31/496* (2013.01); *A61K 47/20* (2013.01)

(58) Field of Classification Search
CPC .. A61K 9/0078; A61K 9/1272; A61K 31/496; A61K 47/20; A61K 47/10;
(Continued)

(56) References Cited

U.S. PATENT DOCUMENTS 8,071,127 B2    12/2011  Cipolla et al.
8,119,156 B2    2/2012   Cipolla et al.
(Continued)

FOREIGN PATENT DOCUMENTS

EP    0223831 B1    7/1992
EP    0267050 B1    9/1994
(Continued)

OTHER PUBLICATIONS

Kistler et al., "Lung transplantation in idiopathic pulmonary fibrosis: a systematic review of the literature" BMC Pulmonary Medicine, 14:139 (2014).
(Continued)

*Primary Examiner* — Gollamudi S Kishore
(74) *Attorney, Agent, or Firm* — Goodwin Procter LLP

(57) ABSTRACT

Provided is a liposomal sustained-release composition for use in treatment of pulmonary disease. The liposomal sustained release composition comprises a liposome that includes a polyethylene glycol (PEG)-modified lipid and encapsulates a tyrosine kinase inhibitor. Tyrosine kinase inhibitor is stably entrapped in the liposome, and the resulting liposomal drug formulation can be aerosolized or nebulized for administration via inhalation. This aerosolized
(Continued)

liposomal drug formulation yields consistent pharmacokinetic and pharmacodynamic profiles while achieving desired efficacy and safety.

17 Claims, 5 Drawing Sheets

(51) Int. Cl.
*A61K 31/496* (2006.01)
*A61K 47/20* (2006.01)

(58) Field of Classification Search
CPC .. A61K 31/4439; A61K 31/47; A61K 31/506; A61K 31/517; A61K 31/4412; A61K 31/404; A61P 11/00
See application file for complete search history.

(56) References Cited

U.S. PATENT DOCUMENTS

| | | | |
|---|---|---|---|
| 8,226,975 | B2 | 7/2012 | Weers |
| 8,652,512 | B2 | 2/2014 | Schmehl et al. |
| 8,802,137 | B2 | 8/2014 | Boni et al. |
| 9,078,897 | B1 | 7/2015 | Cipolla et al. |
| 9,333,214 | B2 | 5/2016 | Gupta |
| 9,408,836 | B2 | 8/2016 | Armendariz Borunda et al. |
| 9,545,401 | B2 | 1/2017 | Cipolla et al. |
| 2010/0239652 | A1* | 9/2010 | Rochlitz ............... A61P 1/04 424/450 |
| 2013/0156851 | A1 | 6/2013 | Cui et al. |
| 2014/0220110 | A1* | 8/2014 | Hayes ............... A61K 38/07 424/450 |
| 2015/0044288 | A1* | 2/2015 | Surber ............... A61K 31/506 424/489 |
| 2015/0064114 | A1 | 3/2015 | Park et al. |
| 2017/0224654 | A1* | 8/2017 | Armstrong ......... A61K 31/4545 |
| 2018/0098945 | A1 | 4/2018 | Nel et al. |

FOREIGN PATENT DOCUMENTS

| | | |
|---|---|---|
| EP | 1658851 A1 | 5/2006 |
| EP | 1438955 B1 | 6/2006 |
| EP | 2079443 B1 | 8/2014 |
| EP | 1530466 B1 | 12/2014 |
| EP | 2363114 B1 | 5/2015 |
| EP | 2384751 B1 | 9/2015 |
| WO | WO-2015/106150 A1 | 7/2015 |
| WO | WO-2016/178064 A1 | 11/2016 |
| WO | 2017053464 * | 3/2017 |
| WO | WO-2017/053464 A1 | 3/2017 |

OTHER PUBLICATIONS

Nalysnyk et al. "Incidence and prevalence of idiopathic pulmonary fibrosis: review of the literature" European Respiratory Review 21(126):355-361 (2012).
Committee for Medicinal Products for Human Use (CHMP), Ofev European Medicines Agency Assessment report, 2014-11-20EMA/76777/2015, Procedure No. EMEA/H/C/003821/0000.
Richeldi et al., "Efficacy and Safety of Nintedanib in Idiopathic Pulmonary Fibrosis" N Engl J Med, 370:2071-2082 (2014).
Corte et al., "Safety, tolerability and appropriate use of nintedanib in idiopathic pulmonary fibrosis", Respiratory Research 16:116 (2015).
Center For Drug Evaluation and Research, Clinical Pharmacology Review NDA#205832, Submitted May 2, 2014.
RxList.com "Ofev (Nintedanib Capsules) Side Effects" <http://www.rxlist.com/ofev-side-effects-drug-center.htm>, downloaded Mar. 11, 2022.
RxList.com "Esbriet (Pirfenidone Capsules)" <https://www.rxlist.com/esbriet-drug.htm>, Downloaded Mar. 11, 2022.
Vib-Mesh Nebulizer HL100, <https://www.healthandlife.com.tw/index.php?action=products_data&id=142&width=1280>, Downloaded Mar. 11, 2022.
Wollin et al., "Mode of action of nintedanib in the treatment of idiopathic pulmonary fibrosis" Eur Respir J, 45:1434-1445 (2015).
Patton et al., "Inhaling medicines: delivering drugs to the body through the lungs" Nature Reviews Drug Discovery; (6):67-74.
Okusanya et al., "Pharmacokinetic and pharmacodynamic evaluation of liposomal amikacin for inhalation in cystic fibrosis patients with chronic pseudomonal infection" Antimicrobial Agents and Chemotherapy, 53(9):3847-3854 (2009).
J P Clancy et al., "Phase II studies of nebulised Arikace in CF patients with Pseudomonas aeruginosa infection" Thorax; 68:818-825 (2013).
Cipolla et al., "Development of Liposomal Ciprofloxacin to Treat Lung Infections" Pharmaceutics 8(6):1-31 (2016).
Schneider et al., "Nanoparticles that do not adhere to mucus provide uniform and long-lasting drug delivery to airways following inhalation" Science Advances; 3:1-10 (2017).
Anabousi et al., "Effect of PEGylation on the stability of liposomes during nebulisation and in lung surfactant" Journal of Nanoscience and Nanotechnology vol. 6, 3010-3016 (2006).
Muralidharan et al., "Inhalable PEGylated Phospholipid Nanocarriers and PEGylated Therapeutics for Respiratory Delivery as Aerosolized Colloidal Dispersions and Dry Powder" *Pharmaceutics*, 6, 333-353 (2014).
Bayard et al., "Polyethylene glycol-drug ester conjugates for prolonged retention of small inhaled drugs in the lung" 171(2): 234-40, J Control Release (2013).
Shen et al., "Distribution and Cellular Uptake of PEGylated Polymeric Particles in the Lung Towards Cell-Specific Targeted Delivery" Pharm Res. 32(10): 3248-3260 (2015).
Zucker et al., "Liposome drugs' loading efficiency: A working model based on loading conditions and drug's physicochemical properties" Journal of Controlled Release, 139(1) pp. 73-80 (2009).
Rouser et al., "Two dimensional thin layer chromatographic separation of polar lipids and determination of phospholipids by phosphorus analysis of spots" Lipids, 5(5):494-496 (1970).
Youn et al., "Improved intrapulmonary delivery of site-specific PEGylated salmon calcitonin: optimization by PEG size selection" J Control Release 68-75, 125(1).

* cited by examiner

INHALABLE LIPOSOMAL SUSTAINED RELEASE COMPOSITION FOR USE IN TREATING PULMONARY DISEASES

CROSS-REFERENCE TO RELATED APPLICATION

This application is a U.S. national stage application under 35 U.S.C. § 371 of International Application No. PCT/US2019/028647, filed Apr. 23, 2019, which claims priority to and the benefit of U.S. Provisional Patent Application No. 62/661,217, filed Apr. 23, 2018, each of which are incorporated herein by reference in their entirety.

BACKGROUND

Technical Field

The present disclosure relates to an inhalable drug delivery system for delivery of a sustained-release liposomal composition. The present disclosure relates to a method of preparing the drug delivery system. The present disclosure also relates to a sustained-release pharmaceutical composition, adapted to a pulmonary delivery system, which has a prolonged duration of efficacy.

Description of Related Art

Undesirable pulmonary diseases are initiated from various external effectors and become overwhelming issues for an aging society. An exemplary pulmonary disease, Idiopathic Pulmonary Fibrosis (IPF) afflicts approximately 3 million people worldwide, with most of the patients being over 50 years old. The prognosis of this disease is poor with the median survival time for IPF patients being 2 to 3 years from diagnosis. IPF is almost an orphan lung disease, with a devastating prognosis and debilitating symptoms with limited treatment options (two approved drugs on the market).

Nintedanib, one tyrosine kinase inhibitor approved for treatment of IPF, is administered at a high dosage of 300 mg per day, which is taken orally as a capsule with a recommended dosage of 150 mg twice a day. In clinical trials, the dosing regimen of such oral tyrosine kinase inhibitor reduced lung function decline (increased forced vital capacity) by approximately 50% when compared to placebo.

However, oral administration of tyrosine kinase inhibitor leads to a very low bioavailability, for instance of nintedanib being 4.7%, in humans. Undesired side effects of oral treatment by the current therapeutic amount of nintedanib include diarrhea (most frequent adverse event), nausea, stomach pain, liver problems, vomiting, decreased appetite, headache, weight loss, and high blood pressure.

Liposomes are self-assembled, fatty acid vesicles composed of phospholipid bilayers with an aqueous interior. These vesicles have been utilized as drug carriers for sustained drug delivery for decades. Liposome encapsulation of a drug alters the pharmacokinetic profile of the free drug, provides slow drug release systemically or at the disease site, allows for high administered doses with less frequent drug administration, and possibly reduces side effects and toxicity. High drug encapsulation inside a liposome can be achieved via a remote loading method (also known as active loading), which relies on transmembrane pH and ion gradients to allow for diffusion of free, uncharged drug molecules into the liposome. While inside the liposome, the free drug molecule can complex with a trapping agent (a counterion) in the aqueous interior to precipitate into a drug-counterion salt that stays inside the liposome. A liposomal drug formulation can be tailored to achieve slow drug release in vivo, which would prolong the therapeutic effect of the drug. This can be accomplished by adjusting the liposome formulation and optimizing certain liposome properties, such as the phospholipids used (different chain lengths, phase transition temperatures), lipid to cholesterol ratio, amount of polyethylene glycol (PEG) on the liposome (to evade clearance by macrophage), trapping agent used for drug encapsulation, and possibly the lamellarity of the liposome.

A drug that has been stably entrapped in a liposome may be aerosolized or nebulized for inhalation delivery. However, it is not readily apparent that utilizing liposome technology to reformulate the tyrosine kinase inhibitor can yield a formulation for inhalation at a therapeutic dose to treat IPF or other pulmonary diseases. Research shows that unpredictable release profiles, plasma half-lives, and bio-distributions are obtained by different administration routes of liposomal drug formulations in vivo. This has been observed among a wide spectrum of active pharmaceutical agents that have been employed for treating pulmonary diseases. Therefore, liposomal drug formulations should be tailored in such a way that administration via inhalation yields consistent pharmacokinetic and pharmacodynamic profiles while achieving desired efficacy and safety.

Currently, there are two inhalable liposomal drug products in development that have reached clinical trials: liposomal amikacin and liposomal ciprofloxacin. Both liposomal antibiotics for inhalation are being investigated for treating multiple respiratory diseases, such as cystic fibrosis (CF), non-CF bronchiectasis, nontuberculous mycobacterial lung disease, and other virulent infections. Both liposomal drug formulations for inhalation therapy are designed for antibiotics to easily access microorganisms or infected tissues by modifying lipid content to be electrically neutral (U.S. Pat. No. 8,226,975) or by adjusting particle size and amount of free ciprofloxacin to attenuate attraction of macrophages (U.S. Pat. No. 8,071,127).

Unfortunately, the existing inhalable liposomal formulations are unable to satisfy the unmet needs for treatment of other pulmonary diseases, such as IPF, which may necessitate a drug product with different target product profiles, including but not limited to deep lung deposition, enhanced mucus penetration, prolonged drug retention in the lung, and increased liposomal drug stability. To date, no relevant studies have reported an inhalable drug effective for treatment of pulmonary disease by tyrosine kinase inhibitor or the like in the form of a lipid-based sustained release composition. Therefore, there is an unmet need for a formulation suitable for treating pulmonary disease, such as IPF: being inhalable, having an improved stability or resistance to destruction by local lung surfactant, and, furthermore, having a dose strength to ensure the potential for reaching the desired efficacy in the pulmonary environment.

SUMMARY

The present disclosure provides an inhalable liposomal drug formulation comprising phospholipid(s), a sterol, a PEG-modified phospholipid, and a tyrosine kinase inhibitor entrapped in the aqueous interior of the liposome. In some embodiments, the entrapped tyrosine kinase inhibitor is a substituted indoline compound. In some embodiments, the substituted indoline compound is nintedanib.

To improve upon existing treatment paradigms of pulmonary diseases, such as pulmonary fibrosis, and to take advantage of the benefits of slow, sustained drug release, we developed a liposomal sustained release composition of tyrosine kinase inhibitor comprising liposome-encapsulated tyrosine kinase inhibitor and a predetermined amount of free tyrosine kinase inhibitor in an aqueous suspension that can be aerosolized and inhaled for enhanced treatment of pulmonary disease. Particularly, there is a need for an inhalable form of nintedanib for IPF treatment.

The present disclosure provides a liposomal sustained release composition of tyrosine kinase inhibitor for use in the treatment of IPF having the advantages of: 1) achieving a therapeutic effect with a much lower drug dose, 2) delivering the drug directly to the disease site, 3) quicker onset of action, 4) reducing adverse drug reactions and systemic effects, 5) bypassing first-pass metabolism observed in oral dosing, thus increasing the bioavailability of the drug (and possibly reducing hepatotoxicity), 6) increasing the residence time of drug in the lung via sustained release from the liposomal drug formulation, 7) decreasing the frequency of drug administration, 8) non-invasive inhalation delivery, and 9) improving patient outcomes and compliance. The inhaled drug dose of the liposomal sustained release composition of tyrosine kinase inhibitor for treating IPF in a form of aerosolized particles can be significantly lower than an oral dose while still achieving similar therapeutic efficacy.

The liposome with the entrapped tyrosine kinase inhibitor according to the present disclosure incorporates a significant amount of PEG moiety to achieve longer, sustained drug release that will be safe, efficacious, and suitable for once-daily or even less frequent dosing.

In some embodiments, the liposomes with the entrapped tyrosine kinase inhibitor comprise phosphocholine (PC): cholesterol at a molar ratio of 1:1 to 3:2, wherein the PC can be hydrogenated soy phosphatidylcholine (HSPC), 1,2-distearoyl-sn-glycero-3-phosphocholine (DSPC), 1,2-dipalmitoyl-sn-glycero-3-phosphocholine (DPPC), or a mixture thereof, such as DSPC and 1,2-dipalmitoyl-sn-glycero-3-phosphoethanolamine (DPPE) at a molar ratio of 1:1.

In some embodiments, the PEG-modified phosphoethanolamine (PE) can be DSPE-PEG2000 and ranges from 0.0001 mol % to 40 mol % of the total lipid content of the liposomes.

In some embodiments, the lipid concentration of the liposomal sustained-release composition ranges from 10 mM to 25 mM and the drug-to-lipid (D/L) ratio ranges from 300 g/mol to 700 g/mol.

In some embodiments, the mean particle diameter of the liposomes with the entrapped tyrosine kinase inhibitor ranges from 100 nm to 300 nm.

In various embodiments, the present disclosure provides an aerosolized composition of particles of liposomal composition comprising liposomes with entrapped tyrosine kinase inhibitor for use in the treatment of idiopathic pulmonary fibrosis (IPF), wherein the liposomes with entrapped tyrosine kinase inhibitor has a drug-to-lipid ratio of at least 200 g/mol.

In another aspect, the present disclosure provides an aerosolized composition of particles of the liposomal sustained release composition for use in the treatment of idiopathic pulmonary fibrosis (IPF), wherein the composition comprises liposomes with the entrapped tyrosine kinase inhibitor having PEG-modified lipid at a predetermined amount, for example but not limited to less than 6 mol % on the basis of the total phospholipids and sterol.

In yet another aspect, the present disclosure provides a method for treating pulmonary disease, which comprises administering a therapeutically effective amount of the tyrosine kinase inhibitor of the aerosolized composition of particles of the liposomal sustained release composition to a subject in need thereof, wherein the therapeutically effective amount of the tyrosine kinase inhibitor ranges from 0.001 mg/kg to 50 mg/kg per body weight of the subject.

Other objectives, advantages, and novel features of the disclosure will become apparent from the following detailed description when taken in conjunction with the accompanying drawings.

DETAILED DESCRIPTION OF THE EMBODIMENTS

Figure 1:
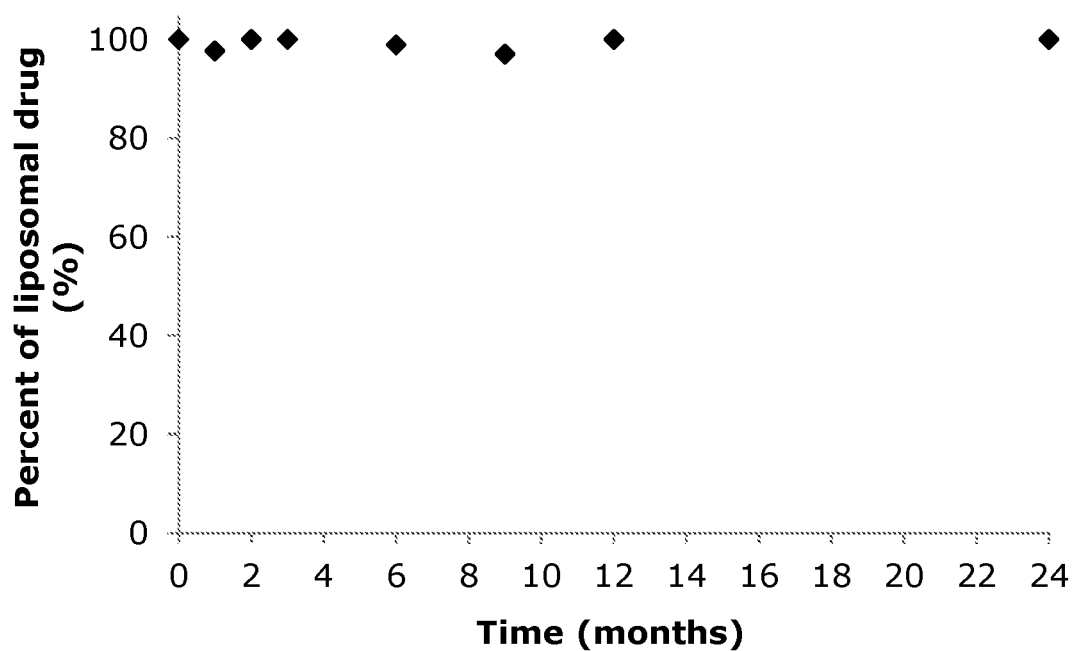
FIG. 1 is a graph showing the storage stability of 300 mM ammonium sulfate (A.S.) liposomal nintedanib at 4° C.

As employed above and throughout the disclosure, the following terms, unless otherwise indicated, shall be understood to have the following meanings.

As used herein, the singular forms "a", "an" and "the" include the plural reference unless the context clearly indicates otherwise.

All numbers herein may be understood as modified by "about," which, when referring to a measurable value such as an amount, a temporal duration, and the like, is meant to encompass variations of ±10%, preferably ±5%, more preferably ±1%, and even more preferably ±0.1% from the specified value, as such variations are appropriate to obtain a desired amount of liposomal drug, unless otherwise specified.

The term "treating," "treated," or "treatment" as used herein includes preventive (e.g., prophylactic), palliative, and curative uses or results.

The term "subject" includes a vertebrate having cancer or other disease(s) affecting pulmonary function. In some embodiments, the subject is a warm-blooded animal, such as a mammal, including a human.

As used herein, the term drug to lipid ratio ("D/L ratio") refers to the ratio of tyrosine kinase inhibitor to total phospholipid content. The tyrosine kinase inhibitor content of free and liposomal drug was determined by UV-Vis absorbance measurements. The phospholipid content, or concentration, of liposome and liposomal drug was determined by assaying the phosphorus content of liposome and liposomal drug samples using a phosphorus assay (adapted from G. Rouser et al., Lipids 1970, 5, 494-496). The D/L ratio can be expressed in terms of either g/mol or mol/mol. For example, g/mol of liposomal nintedanib can be converted to mol/mol of liposomal nintedanib by dividing the g/mol value by 539.62 to yield the mol/mol value.

As used herein, the term mol % means the percentage of moles of a given component of a mixture relative to the total moles of that mixture.

Liposome

The term "liposome" as used herein refers to a particle characterized by having an aqueous interior space sequestered from an outer medium by a membrane of one or more bilayer membranes forming a vesicle. Bilayer membranes of liposomes are typically formed by lipids, i.e., amphiphilic molecules of synthetic or natural origin that comprise spatially separated hydrophobic and hydrophilic domains. In certain embodiments of the present disclosure, the term "liposomes" refers to small unilamellar vesicle (SUV) liposomes in which one lipid bilayer forms the membrane.

In general, liposomes comprise a lipid mixture typically including one or more lipids selected from the group consisting of: dialiphatic chain lipids, such as phospholipids, diglycerides, dialiphatic glycolipids, single lipids such as sphingomyelin and glycosphingolipid, steroids such as cholesterol and derivatives thereof, and combinations thereof.

Examples of phospholipids according to the present disclosure include, but are not limited to, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-stearoyl-sn-glycero-3-phosphocholine (PSPC), 1-palmitoyl-2-oleoyl-sn-glycero-3-phosphatidylcholine (POPC), 1,2-distearoyl-sn-glycero-3-phosphocholine (DSPC), 1,2-dioleoyl-sn-glycero-3-phosphocholine (DOPC), hydrogenated soy phosphatidylcholine (HSPC), 1,2-dimyristoyl-sn-glycero-3-phospho-(1'-rac-glycerol) (sodium salt) (DMPG), 1,2-dipalmitoyl-sn-glycero-3-phospho-(1'-rac-glycerol) (sodium salt) (DPPG), 1-palmitoyl-2-stearoyl-sn-glycero-3-phospho-(1'-rac-glycerol) (sodium salt) (PSPG), 1,2-distearoyl-sn-glycero-3-phospho-(1'-rac-glycerol) (sodium salt) (DSPG), 1,2-dioleoyl-sn-glycero-3-phospho-(1'-rac-glycerol) (DOPG), 1,2-dimyristoyl-sn-glycero-3-phospho-L-serine (sodium salt) (DMPS), 1,2-dipalmitoyl-sn-glycero-3-phospho-L-serine (sodium salt) (DPPS), 1,2-distearoyl-sn-glycero-3-phospho-L-serine (sodium salt) (DSPS), 1,2-dioleoyl-sn-glycero-3-phospho-L-serine (DOPS), 1,2-dimyristoyl-sn-glycero-3-phosphate (sodium salt) (DMPA), 1,2-dipalmitoyl-sn-glycero-3-phosphate (sodium salt) (DPPA), 1,2-distearoyl-sn-glycero-3-phosphate (sodium salt) (DSPA), 1,2-dioleoyl-sn-glycero-3-phosphate (sodium salt) (DOPA), 1,2-dipalmitoyl-sn-glycero-3-phosphoethanolamine (DPPE), 1-palmitoyl-2-oleoyl-sn-glycero-3-phosphoethanolamine (POPE), 1,2-distearoyl-sn-glycero-3-phosphoethanolamine (DSPE), 1,2-dioleoyl-sn-glycero-3-phosphoethanolamine (DOPE), 1,2-dipalmitoyl-sn-glycero-3-phospho-(1'-myo-inositol) (ammonium salt) (DPPI), 1,2-distearoyl-sn-glycero-3-phosphoinositol (ammonium salt) (DSPI), 1,2-dioleoyl-sn-glycero-3-phospho-(1'-myo-inositol) (ammonium salt) (DOPI), cardiolipin, L-a-phosphatidylcholine (EPC), and L-α-phosphatidylethanolamine (EPE).

Polyethylene Glycol (PEG)-Modified Lipid

A polyethylene glycol-modified lipid comprises a polyethylene glycol moiety conjugated with a lipid. In some embodiments, the PEG moiety has a molecular weight from about 1,000 to about 20,000 daltons. In some embodiments, the PEG-modified lipid is mixed with the phospholipids to form liposomes with one or more bilayer membranes. In some embodiments, the amount of PEG-modified lipid ranges from 0.0001 mol % to 40 mol %, optionally from 0.001 mol % to 30 mol %, and optionally from 0.01 mol % to 20 mol %, on the basis of the total phospholipids and sterol. In some embodiments, the amount of PEG-modified lipid is no more than 6 mol %, no more than 5 mol %, no more than 3 mol %, or no more than 2 mol %, on the basis of the total phospholipids and sterol. In some embodiments, the PEG-modified lipid has a PEG moiety with an average molecular weight ranging from 1,000 g/mol to 5,000 g/mol. In some embodiments, the PEG-modified lipid is phosphatidylethanolamine linked to a polyethylene glycol group (PEG-PE). In some embodiments, PEG-modified phosphatidylethanolamine is 1,2-distearoyl-sn-glycero-3-phosphoethanolamine-N-[methoxy(polyethylene glycol)] (DSPE-PEG).

Liposomal Sustained Release Compositions

The terms "liposomal drug formulation" and "liposomal sustained release composition" are interchangeably used in the present disclosure. The liposomal sustained release composition in accordance with the present disclosure includes, but is not limited to, liposomes with entrapped tyrosine kinase inhibitor prepared by entrapping the tyrosine kinase inhibitor in the aqueous interior of the liposome via a transmembrane pH gradient-driven remote loading method. In some embodiments, the transmembrane pH gradient is created by using a trapping agent for remote loading of the tyrosine kinase inhibitor into liposomes. In various embodiments, the trapping agent is selected from the group consisting of ammonium sulfate, ammonium mesylate, ammonium tosylate, triethylammonium sucrose octasulfate, and combinations thereof.

In certain embodiments, the liposome with the entrapped tyrosine kinase inhibitor comprises (a) a lipid bilayer comprising one or more phospholipids, a sterol, and a polyethylene glycol (PEG)-modified lipid, including but not limited to a PEG-modified phosphatidylethanolamine; and (b) an aqueous interior encompassed by the lipid bilayer entrapping a tyrosine kinase inhibitor.

In some embodiments, the one or more phospholipids is a neutral phospholipid. In some embodiments, the PEG-modified lipid is DSPE-PEG and the amount of DSPE-PEG in the liposome ranges from 0.001 mol % to 5 mol % on the basis of the total phospholipid and sterol.

In some embodiments, the liposomes with the entrapped tyrosine kinase inhibitor have a mean particle diameter between 50 nm and 400 nm.

The term "tyrosine kinase inhibitors" (TKIs) refers to one or more groups of substances inhibiting tyrosine kinases, enzymes responsible for the activation of many proteins by adding a phosphate group to the protein (phosphorylation). In some embodiments, the term TKI includes but is not limited to indoline compound. In some embodiments, the TKI is a substituted indoline compound such as nintedanib or pharmaceutically acceptable salts thereof.

In some embodiments, the tyrosine kinase inhibitor in accordance with the present disclosure is selected from the group consisting of nintedanib, saracatinib, axitinib, cabozantinib, pazopanib, vandetanib, regorafenib, sorafenib, sunitinib, imatinib, bosutinib, dasatinib, nilotinib, ponatinib, afatinib, erlotinib, gefitinib, lapatinib, crizotinib and ruxolitinib.

In some embodiments, the tyrosine kinase inhibitor in accordance with the present disclosure is nintedanib, wherein 180.6 mg of nintedanib esylate is equivalent to 150 mg of nintedanib base.

In some embodiments, the tyrosine kinase inhibitor in accordance with the present disclosure is a substituted indoline compound, referring to an indole compound with one or more substituted groups, which target vascular endothelial growth factor receptor (VEGFR), fibroblast growth factor receptor (FGFR), and platelet derived growth factor receptor (PDGFR).

In some embodiments, the substituted indoline compound is selected from the group consisting of:

(a) 3-Z-[1-(4-(piperidin-1-yl-methyl)-anilino)-1-phenyl-methylene]-6-ethoxycarbonyl-2-indolinone, (b) 3-Z-[(1-(4-(piperidin-1-yl-methyl)-anilino)-1-phenyl-methylene]-6-carbamoyl-2-indolinone, (c) 3-Z-[1-(4-(piperidin-1-yl-methyl)-anilino)-1-phenyl-methylene]-6-methoxycarbonyl-2-indolinone, (d) 3-Z-[1-(4-(dimethylaminomethyl)-anilino)-1-phenyl-methylene]-6-ethoxycarbonyl-2-indolinone, (e) 3-Z-[1-(4-((2,6-dimethyl-piperidin-1-yl)-methyl)-anilino)-1-phenyl-methylene]-6-ethoxycarbonyl-2-indolinone, (f) 3-Z-[1-(4-(N-(2-dimethylamino-ethyl)-N-acetyl-amino)-anilino)-1-phenyl-methylene]-6-ethoxycarbonyl-2-indolinone, (g) 3-Z-[1-(4-(N-(3-dimethylamino-propyl)-N-acetyl-amino)-anilino)-1-phenyl-methylene]-6-ethoxycarbonyl-2-indolinone, (h) 3-Z-[1-(4-(N-(2-dimethylamino-ethyl)-N-methylsulphonyl-amino)-anilino)-1-phenyl-methylene]-6-ethoxycarbonyl-2-indolinone, (i) 3-Z-[1-(4-(dimethylaminomethyl)-anilino)-1-phenyl-methylene]-6-methoxycarbonyl-2-indolinone, (j) 3-Z-[1-(4-(N-acetyl-N-dimethylaminocarbonylmethyl-amino)-anilino)-1-phenyl-methylene]-6-methoxycarbonyl-2-indolinone, (k) 3-Z-[1-(4-ethylaminomethyl-anilino)-1-phenyl-methylene]-6-methoxycarbonyl-2-indolinone, (l) 3-Z-[1-(4-(1-methyl-imidazol-2-yl)-anilino)-1-phenyl-methylene]-6-methoxycarbonyl-2-indolinone, (m) 3-Z-[1-(4-(N-dimethylaminomethylcarbonyl-N-methyl-amino)-anilino)-1-phenyl-methylene]-6-methoxycarbonyl-2-indolinone, (n) 3-Z-[1-(4-(N-(2-dimethylamino-ethyl)-N-methylsulphonyl-amino)-anilino)-1-phenyl-methylene]-6-methoxycarbonyl-2-indolinone, (o) 3-Z-[1-(4-(N-(3-dimethylamino-propyl)-N-methylsulphonyl-amino)-anilino)-1-phenyl-methylene]-6-methoxycarbonyl-2-indolinone, (p) 3-Z-[1-(4-(N-dimethylaminocarbonylmethyl-N-methylsulphonyl-amino)-anilino)-1-phenyl-methylene]-6-methoxycarbonyl-2-indolinone, (q) 3-Z-[1-(4-(N4(2-dimethylamino-ethyl)-carbonyl)-N-methyl-amino)-anilino)-1-phenyl-methylene]-6-methoxycarbonyl-2-indolinone, (r) 3-Z-[1-(4-(N-(2-dimethylamino-ethyl)-N-acetyl-amino)-anilino)-1-phenyl-methylene]-6-methoxycarbonyl-2-indolinone, (s) 3-Z-[1-(4-methylaminomethyl-anilino)-1-phenyl-methylene]-6-methoxycarbonyl-2-indolinone, (t) 3-Z-[1-(4-(N-((4-methyl-piperazin-1-yl)-methylcarbonyl)-N-methyl-amino)-anilino)-1-phenyl-methylene]-6-methoxycarbonyl-2-indolinone, and (u) methyl (3Z)-3-[[4-[methyl-[2-(4-methylpiperazin-1-yl)acetyl]amino]anilino]-phenylmethylidene]-2-oxo-1H-indole-6-carboxylate.

Aerosolized Particles of the Liposomal Sustained Release Composition

The liposomal sustained release composition in accordance with the present disclosure can be adapted for the preparation of an aerosolized composition of particles. In some embodiments, the liposome with the entrapped tyrosine kinase inhibitor comprises (a) a lipid bilayer comprising a phospholipid, a sterol, and a PEG-modified phosphatidylethanolamine; and (b) an aqueous interior encompassed by the lipid bilayer and containing a tyrosine kinase inhibitor, and wherein drug leakage of the tyrosine kinase inhibitor from the liposome after aerosolization is less than 10%.

In some embodiments, the liposomal sustained release composition of tyrosine kinase inhibitor for use according to the present disclosure has a lipid concentration ranging from 1 mM to 25 mM. In certain embodiments, the liposomal sustained release composition of tyrosine kinase inhibitor for use according to the present disclosure has a concentration of the tyrosine kinase inhibitor ranging from 1 mg/mL to 15 mg/mL. In various embodiments, the liposomal sustained release composition of tyrosine kinase inhibitor for use according to the present disclosure has a drug-to-phospholipid ratio ranging from 100 g drug/mol phospholipid to 1,000 g drug/mol phospholipid, optionally 500 g drug/mol phospholipid to 1000 g drug/mol phospholipid, and optionally 0.01 mol drug/mol phospholipid to 2.5 mol drug/mol phospholipid, 0.05 mol drug/mol phospholipid to 2 mol drug/mol phospholipid, 0.1 mol drug/mol phospholipid to 1.5 mol drug/mol phospholipid and 0.5 mol drug/mol phospholipid to 1.5 mol drug/mol phospholipid.

In some embodiments, the free tyrosine kinase inhibitor of the liposomal sustained release composition is present in an amount less than 50%, optionally ranging from 0.5% to 40%, from 1% to 30%, from 2% to 20%, or from 3% to 10% of the total amount (i.e., free plus liposome-encapsulated) of the tyrosine kinase inhibitor of the liposomal sustained release composition.

In some embodiments, an aerosolized composition of particles is generated from the liposomal sustained release composition by using a nebulizer. In certain embodiments, the nebulizer is selected from the group consisting of an air-jet nebulizer, an ultrasonic nebulizer, and a vibrating mesh nebulizer.

In some embodiments, the aerosolized composition of particles has a mass median aerodynamic diameter between 0.5 μm and 5 μm.

In some embodiments, the aerosolized composition of particles is administered at an amount of 0.001 mg/kg to 50 mg/kg, 0.005 mg/kg to 40 mg/kg, 0.01 mg/kg to 30 mg/kg, 0.05 mg/kg to 20 mg/kg, 0.1 mg/kg to 10 mg/kg or 0.5 mg/kg to 5 mg/kg per body weight of a subject by pulmonary delivery to the subject to achieve a release rate between about 0.5% and 25% of the administered tyrosine kinase inhibitor dose per hour, with complete release of the tyrosine kinase inhibitor occurring after a minimum of about 12 hours.

Pulmonary Diseases

Pulmonary diseases in accordance with the present disclosure are embodied in non-infectious pulmonary diseases.

The non-infectious pulmonary diseases refer to lung related disorders excluding pulmonary infection caused by gram negative bacterium. In some embodiments, the pulmonary diseases include, but are not limited to: pulmonary fibrosis (such as idiopathic pulmonary fibrosis or radiation therapy-induced fibrosis), lung cancer (such as non-small cell lung cancer), or systemic sclerosis (also known as scleroderma). The term "Idiopathic Pulmonary Fibrosis" (IPF) refers to a type of chronic lung disease characterized by a progressive and irreversible decline in lung function. IPF belongs to a family of lung disorders known as interstitial lung diseases (ILDs) or, more accurately, diffuse parenchymal lung diseases. Within this category of diffuse lung diseases, IPF belongs to the subgroup known as idiopathic interstitial pneumonia (IIP). There are seven distinct IIPs, differentiated by specific clinical features and pathological patterns. IPF is the most common form of IIP. Symptoms of IPF typically include gradual onset of shortness of breath and a dry cough. Other symptoms of IPF may include feeling tired and nail clubbing. Exercise-induced breathlessness and chronic dry cough may be prominent symptoms of IPF as well. Complications of IPF include pulmonary hypertension, heart failure, pneumonia, and pulmonary embolism.

The disclosure will be further described with reference to the following specific, non-limiting examples.

EXAMPLES

The following examples illustrate the preparation and properties of certain embodiments of the present disclosure.

Example 1

Preparation of Liposomal Tyrosine Kinase Inhibitor (TKI)
I. Preparation of Empty Liposomes Liposomes were prepared via the thin-film hydration method or solvent injection method. The process for preparing empty liposomes by thin-film hydration method comprises the following steps:
1. weighing out a lipid mixture of phospholipids and cholesterol at a predetermined molar ratio either in the presence or absence of DSPE-PEG2000 and adding the lipid mixture to 10 mL of chloroform in a round-bottom flask;
2. placing the flask in a rotary evaporator at 60° C. and stirring the flask to dissolve the lipid mixture, followed by putting the flask under vacuum while stirring to evaporate the chloroform to obtain a dried lipid film;
3. preparing a trapping agent solution (e.g., ammonium sulfate (A.S.)) by adding a trapping agent to 5 mL of distilled water and vortexing the solution to dissolve the powder;
4. adding the trapping agent solution to the dried lipid film and stirring it at 60° C. for 30 minutes to form a proliposome solution;
5. freeze-thawing the proliposome solution 5 times with liquid nitrogen and a 60° C. water bath to obtain a liposome sample;
6. extruding the liposome sample 10 times through a 0.2 μm polycarbonate membrane at 60° C., then 10 times through a 0.1 μm polycarbonate membrane at 60° C.;
7. dialyzing the extruded liposome sample to remove free trapping agent, followed by adding the sample to a dialysis bag (MWCO: 25 kDa), sealing the bag, and stirring the dialysis bag in 100× volume of a 9.4% (w/v) sucrose solution; and further replacing the sucrose solution after 1 hour and after 4 hours, and letting the dialysis bag stir overnight; and
8. sterilizing the dialyzed liposome sample by filtering it through a 0.45 μm polytetrafluoroethylene (PTFE) membrane to obtain the empty liposomes.

The various liposome formulations that were prepared for forming the empty liposomes to be used for loading tyrosine kinase inhibitor (e.g. nintedanib) are listed in Table 1 below (all liposome formulations were prepared in a 9.4% (w/v) sucrose solution). For liposome formulations comprising both DSPC and DPPE lipids, steps #4-6 were performed at 70° C. instead of 60° C. due to DPPE having a relatively high $T_m$ of 63° C. The mean particle diameter of these liposomes was approximately 120 nm.

TABLE 1

Liposome Formulations

| Formulation no. | Molar ratio | | | | Cholesterol | Trapping agent |
|---|---|---|---|---|---|---|
| | Phospholipids | | | | | |
| | HSPC | DSPC | DPPE | DSPE-PEG2000 | | |
| 1 | 3 | 0 | 0 | 0 | 2 | 300 mM |
| 2 | 3 | 0 | 0 | 0.045 | 2 | A.S. |
| 3 | 3 | 0 | 0 | 0.1 | 2 | |
| 4 | 3 | 0 | 0 | 0.15 | 2 | |
| 5 | 3 | 0 | 0 | 0.26 | 2 | |
| 6 | 0 | 3 | 0 | 0.045 | 2 | |
| 7 | 0 | 3 | 0 | 0.26 | 2 | |
| 8 | 0 | 3 | 3 | 0.09 | 4 | |
| 9 | 0 | 3 | 3 | 0.526 | 4 | |

II. Drug Loading of TKI into Liposomes to Obtain Liposomal TKI

The following method is an exemplary protocol for the encapsulation of TKI (i.e. nintedanib) in liposomes by remote loading, which comprises the steps of:

1. preparing solutions of 9.4% (w/v) sucrose and 9.4% (w/v) sucrose buffer containing 31 mg/mL L-histidine (L-His), pH 6.5;
2. preparing a solution of 15 mg/mL nintedanib ethanesulfonate in 9.4% (w/v) sucrose and briefly heating the solution at 60° C. to obtain a stock solution comprising nintedanib (hereafter denoted as Nin stock solution);
3. mixing together in a conical tube: (a) empty liposomes as prepared by the process according to Part I of Example 1 (in some embodiments, with the condition of DSPC:cholesterol:DSPE-PEG2000 at a molar ratio of 3:2:0.045, 300 mM ammonium sulfate (A.S.), and 58.27 mM lipid concentration), (b) a 9.4% (w/v) sucrose solution, (c) a 9.4% (w/v) sucrose buffer containing 31 mg/mL L-His, pH 6.5, and (d) Nin stock solution, to obtain a loading solution. In some embodiments, the loading solution has a D/L ratio of 500 g/mol. In one embodiment, the empty liposomes, sucrose solution, sucrose buffer, and Nin stock solution are mixed together as provided in Table 2, below;
4. shaking the loading solution vigorously in a 60° C. water bath and incubating at 60° C. for 15 minutes to form the liposomal drug sample, followed by placing the liposomal drug sample on ice for a few minutes;
5. dialysis by adding the chilled liposomal drug sample into a dialysis bag (MWCO: 25 kDa), sealing the bag, and stirring the dialysis bag in 100× volume of a 9.4% (w/v) sucrose solution; and replacing the sucrose solution after 1 hour and after 4 hours, and letting the dialysis bag stir overnight; and
6. determining the drug encapsulation (i.e. loading efficiency) of the final sample using size-exclusion column chromatography and HPLC analysis (drug concentrations of all samples, liposomal or total form, were determined by absorbance measurements at 388 nm).

TABLE 2

Exemplary conditions for remote loading of TKI into liposome

| Final target lipid concentration (mM) | Empty liposome volume | 9.4% (w/v) sucrose | 9.4% (w/v) sucrose buffer with 31 mg/mL L-His, pH 6.5 | 15 mg/mL Nin stock solution | Final pH of loading solution |
|---|---|---|---|---|---|
| 15 | 772.2 µL | 277.8 µL | 150 µL | 1,800 µL | 6.0 to 6.5 |

Example 2

Entrapment of TKI in Liposome

Embodied TKI, nintedanib, was loaded into empty liposomes with a mean particle diameter of approximately 120 nm and comprising various phospholipids (e.g., HSPC, DSPC, DSPC/DPPE, or combinations thereof), with 300 mM A.S. as the trapping agent, and the indicated content of PEG-modified phospholipid (e.g., 0.9 mol % DSPE-PEG2000) according to the method described in Example 1, section II.

Table 3 summarizes the nintedanib encapsulation results for these active loading experiments. The 300 mM A.S. empty liposomes comprising 0.9 mol % PEG-modified lipid encapsulated a D/L ratio of at least 0.9 mol/mol of nintedanib, regardless of the PC lipids or combination of PC/PE lipids in the empty liposome formulation. Therefore, for liposomes comprising the same trapping agent (ammonium sulfate) and PEG content, there is flexibility in choosing different phospholipids for an inhalable liposomal nintedanib formulation that can achieve high drug encapsulation, desired sustained release, and prolonged drug retention in the pulmonary environment.

TABLE 3

Nintedanib encapsulation results for ~120 nm liposomes comprising various phospholipids and 0.9 mol % PEG-modified lipid

| Liposome composition (molar ratio) | Total drug concentration (mg/mL) | Total D/L ratio (mol/mol) | Loading efficiency (%) | Liposomal D/L ratio (mol/mol) |
|---|---|---|---|---|
| HSPC:cholesterol:DSPE-PEG2000 3:2:0.045 | 9.22 | 1.47 | 66.0 | 0.97 |
| | 7.35 | 0.92 | 106 | 0.98 |
| DSPC:cholesterol:DSPE-PEG2000 3:2:0.045 | 7.48 | 0.93 | 103 | 0.96 |
| DSPC:DPPE:cholesterol:DSPE-PEG2000 3:3:4:0.09 | 7.80 | 1.02 | 98.0 | 1.00 |

Example 3

Effect of Empty Liposome Size on the Stability of Nebulized Liposomal TKI

The stability of liposomal TKI after nebulization was investigated for liposomal drugs of varying particle sizes for formulations of low PEG content with high encapsulation of nintedanib. Different sized liposomes were prepared by extrusion of hydrated lipids through polycarbonate membranes of varying pore sizes (0.1 µm, 0.2 µm, 0.4 µm, and 1 µm) prior to remote loading of nintedanib into said liposomes. The liposome formulation used for the nebulization stability tests had a composition of HSPC:cholesterol:DSPE-PEG2000 at a molar ratio of 3:2:0.045 with 300 mM A.S. as the trapping agent. The protocol for nebulization of the liposomal TKI sample was as follows:

1. add 2 mL of liposomal drug to the medication chamber of a Vib-Mesh Nebulizer HL100 (commercialized by Health and Life Corporation);
2. slide in and connect the medication chamber to the rest of the nebulizer;
3. turn on the nebulizer to begin aerosolization of the sample and nebulize the entire 2 mL sample (total nebulization time was almost 6 minutes);
4. collect the aerosol particles in a 50-mL conical tube that is firmly connected to the nebulizer outlet and sealed with parafilm; and
5. determine the drug loading efficiency of the liposomal drug sample prior to and after nebulization using size-exclusion column chromatography and HPLC analysis.

The results of the nebulization stability tests are shown in Table 4 below. Liposomal drug formulations comprising liposomes with mean particle diameters below 300 nm were very stable with practically no drug leakage (≤1%). Liposomal formulations of drug with mean particle diameters slightly larger than 300 nm had a small amount of drug leakage (about 5%). Overall, aerosolized particles of the liposomal drug formulation in which liposomes had mean particle diameters in the 100 nm to 300 nm range were stable, as drug leakage was minimal and particle size did not change significantly before and after nebulization.

TABLE 4

Nebulization stability of liposomal nintedanib

| Membrane pore size used to extrude empty liposome (µm) | Liposomal TKI mean particle diameter (nm) | | Nebulized liposomal TKI drug-to-lipid (D/L) ratio (mol/mol) | | TKI leakage (%) |
|---|---|---|---|---|---|
| | Pre-nebulization | Post-nebulization | Free + liposomal | Liposomal | |
| 0.1 | 128 | 128 | 0.92 | 0.92 | 0 |
| 0.2 | 191 | 189 | 0.91 | 0.90 | 1.1 |
| 0.4 | 244 | 244 | 0.93 | 0.93 | 0 |
| 1 | 322 | 311 | 1.03 | 0.98 | 4.9 |

Example 4

Storage Stability of Liposomal Drug Formulations

Figure 2:
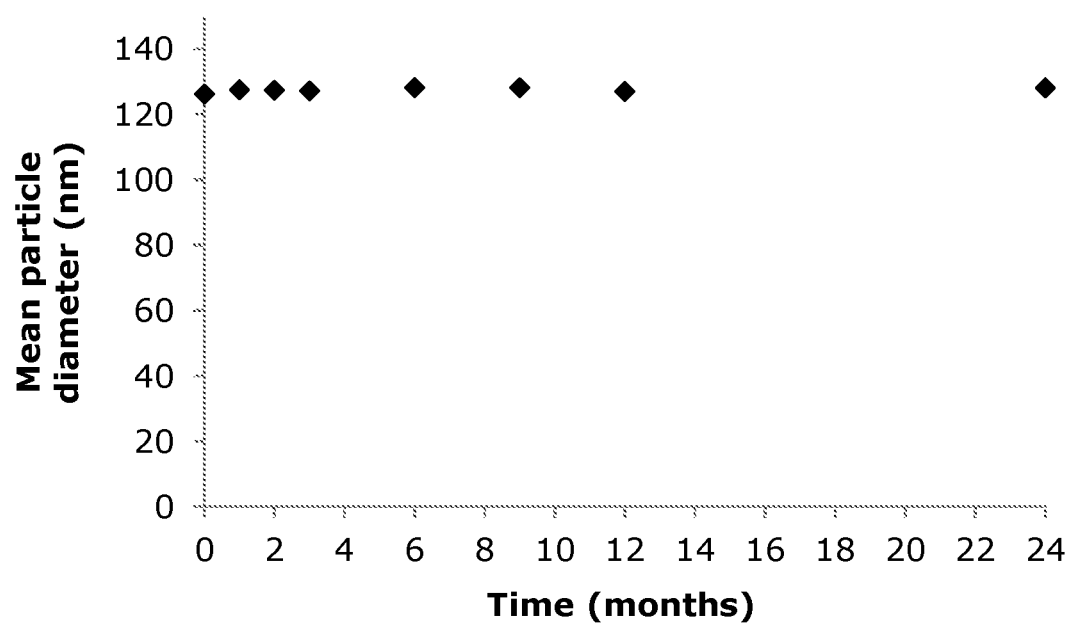
FIG. 2 is a graph showing the particle size of 300 mM ammonium sulfate (A.S.) liposomal nintedanib stored at 4° C.

The stability of liposomal TKI stored at 4° C. was monitored for two years. Nintedanib was remotely loaded into liposomes comprising HSPC:cholesterol:DSPE-PEG2000 at a molar ratio of 3:2:0.045 (0.9 mol % PEG-modified lipid) with 300 mM A.S. as the trapping agent. After loading the drug into liposomes, the liposomal drug sample was stirred and dialyzed in 100× volume of a 9.4% (w/v) sucrose solution. The sucrose solution was replaced after 1 hour and after 4 hours, and the sample was stirred in solution overnight. The drug encapsulation (D/L ratio) for the liposome was about 0.9 mol/mol. After storage of the dialyzed liposomal drug sample at 4° C. for two years, practically no encapsulated drug (≤3%) had leaked out of the liposome (FIG. 1). In addition, the particle size of the liposomal TKI suspension remained the same (diameter within ±1 nm) throughout the two-year storage period at 4° C. (FIG. 2).

Example 5

In Vitro Drug Release in Simulated Lung Fluid

The drug release profiles of two liposomal TKI formulations, with 0.45 mol % PEG-modified lipid or 1.75 mol % PEG-modified lipid, were assessed in simulated lung fluid (SLF) to demonstrate their sustained release properties. The two liposomal TKI samples were prepared at about the same nintedanib concentration (3.85 to 3.95 mg/mL drug) with almost no free drug present in either sample (Table 5). The protocol for the in vitro release (IVR) experiments was as follows:

1. dilute each liposomal TKI sample 10-fold by mixing 0.5 mL of each sample with 4.5 mL of SLF (pre-warmed at 37° C.) and placing the diluted sample in a 15-mL centrifuge tube;
2. place the centrifuge tubes, with the diluted samples, into the sample wells of an Intelli-mixer rotator, which is incubating at 37° C. and rotating at 20 rpm;
3. sample 1 mL of the diluted liposomal TKI sample at predetermined time points (e.g., 0, 4, and 24 hours);
4. determine the encapsulation efficiency, wherein the analytical method for determining the encapsulation efficiency of each 1 mL sample was as follows:
   a. pack and wash a 2 mL of Sepharose® CL-4B column with a 9.4% sucrose solution (less than 5 mL);
   b. add 0.1 mL of the sample to the column, then add 0.15 mL of a 9.4% sucrose solution three separate times and wait for the solution to elute from the column;
   c. add 1 mL of a 9.4% sucrose solution to the column and collect the eluent (liposomal drug fraction) in a 10-mL volumetric flask; add methanol to the volumetric flask to bring it up to volume and mix it well (this is the liposomal drug form);
   d. in a separate 10-mL volumetric flask, add 0.1 mL of the unpurified sample to the flask and add methanol to the volumetric flask to bring it up to volume and mix it well (this is the total drug form);
   e. measure the absorbance of the final, diluted samples at 380 nm using a UV-Vis plate reader to determine the drug concentrations of each sample.
5. The encapsulation efficiency (EE) is defined as the liposomal form (LF) of the drug divided by the total form (TF) of the drug: EE(%)=LF/TF*100%.

TABLE 5

Encapsulation results for IVR samples

| Sample name | Drug form | Drug concentration (mg/mL) | EE (%) |
|---|---|---|---|
| AS300 mM/Nin3.74 mg/mL/PEG0.45 mol % | LF | 3.85 | 98.2 |
|  | TF | 3.92 |  |
| AS300 mM/Nin3.74 mg/mL/PEG1.75 mol % | LF | 3.88 | 98.2 |
|  | TF | 3.95 |  |

Figure 3:
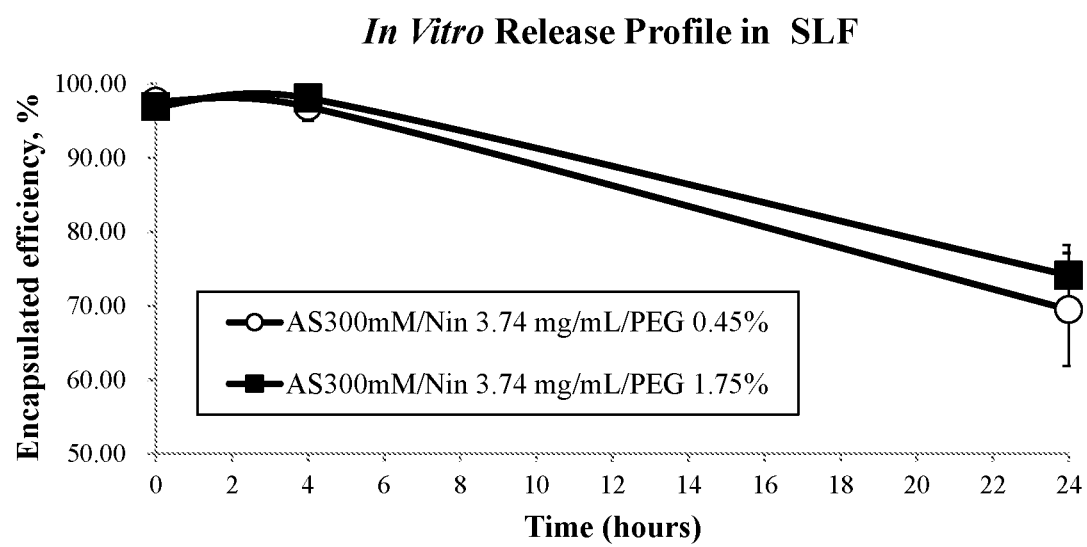
FIG. 3 is a graph depicting the in vitro release profiles of liposomal TKI formulations in simulated lung fluid (SLF); AS=ammonium sulfate; open circle=liposomal TKI formulation comprising 300 mM AS, 3.74 mg/mL nintedanib, and 0.45 mol % PEG-modified lipid; closed square=liposomal TKI formulation comprising 300 mM AS, 3.74 mg/mL nintedanib, and 1.75 mol % PEG-modified lipid; error bars represent the standard deviation.

The IVR profiles of two liposomal TKI formulations are shown in FIG. 3. Liposome formulations retained a significant percentage of the total drug content and exhibited slow drug release over a 24-hour time period. Liposomes with PEG were very stable, as almost no nintedanib was released into SLF in the first four hours and only up to 30% of their total drug content was released into SLF over a 24-hour time period. These IVR results indicate that our liposomal drug formulations can achieve sustained release in vivo in the pulmonary environment.

Example 6

Prolonged Lung Retention and Reduced Drug Toxicity of Liposomal TKI in Healthy Animals A lung retention study of liposomal TKI in healthy mice was conducted to compare the residence times of free form versus liposomal TKI formulations in the mouse lung. Four compositions were used in the study:
1) blank (saline);
2) free nintedanib (drug dissolved in a 9.4% (w/v) sucrose solution);
3) 300 mM A.S. liposomal nintedanib (0.45 mol % PEG); and
4) 300 mM A.S. liposomal nintedanib (1.75 mol % PEG).
The drug concentration of compositions #2-4 was the same: about 3.74 mg/mL nintedanib.

The protocol for the retention study was as follows:
1. anesthetize 7-week old C57BL/6 mice with isoflurane;
2. intratracheally (IT) administer 50 μL of the composition into anesthetized mice using a micro-sprayer (HRH-MAG4);
3. anesthetize and sacrifice mice at predetermined time points (e.g., 2, 6, and 24 hours);
4. at the same predetermined time points (e.g., 2, 6, and 24 hours), collect lung tissue samples for drug determination;
5. analyze nintedanib in lung tissue by:
a) homogenize each lung tissue sample at 6,000 rpm twice (2 runs/cycle) with 1 mL of methanol;
b) centrifuge each sample at 20,000 g for 10 minutes at 4° C.;
c) transfer 0.5 mL of each supernatant into a 5-mL volumetric flask and bring it up to volume with methanol;
d) measure the absorbance of the final, diluted sample at 380 nm using a UV-Vis plate reader to determine the drug concentration of the sample.

Figure 4:
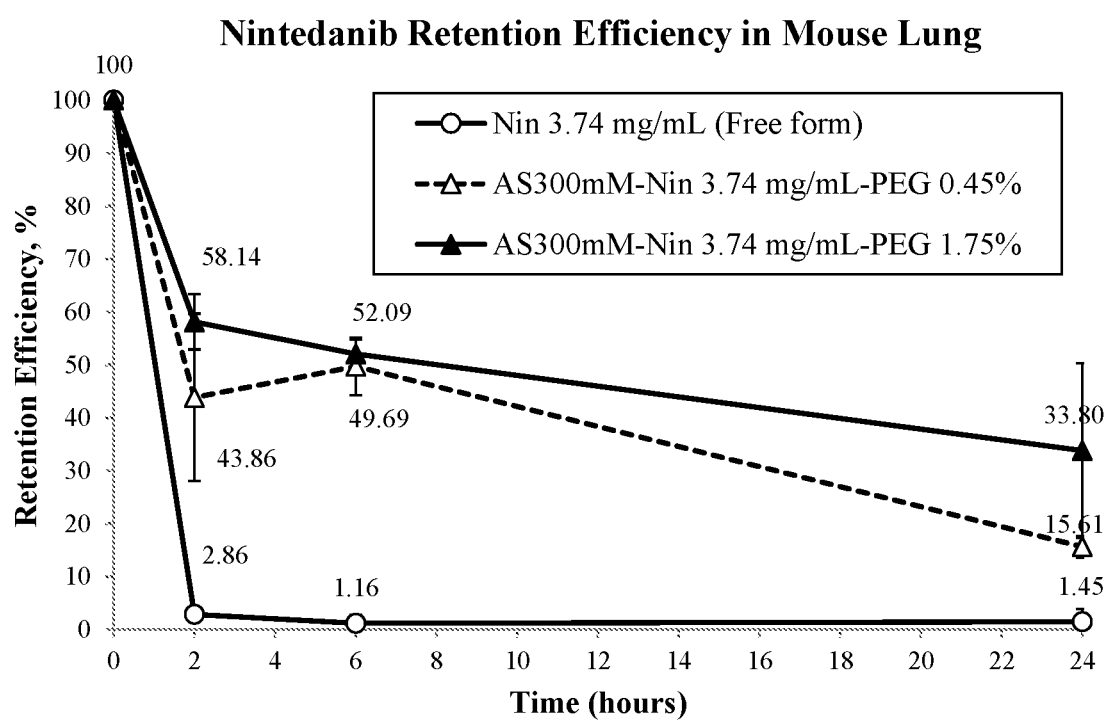
FIG. 4 is a graph depicting the retention of nintedanib (Nin) in lung tissue of healthy mice; AS=ammonium sulfate; open circle=3.74 mg/mL free form nintedanib (Nin); open triangle=liposomal TKI formulation comprising 300 mM AS, 3.74 mg/mL nintedanib, and 0.45 mol % PEG-modified lipid; closed triangle=liposomal TKI formulation comprising 300 mM AS, 3.74 mg/mL nintedanib, and 1.75 mol % PEG-modified lipid; error bars represent the standard deviation.

The results from the lung retention study are shown in FIG. 4. For free nintedanib (free drug dissolved in an aqueous solution) administered intratracheally, almost none of the drug was retained in the lung after just two hours. Thus, nearly all of the drug was absorbed and cleared from the lung within that short time period. In contrast, animals administered liposomal nintedanib (comprising either 0.45 mol % or 1.75 mol % PEG-modified lipid) retained about half of the total drug dose in the lung six hours after IT administration. Furthermore, from 16% to over 30% of the total dose was still observed in the lung after 24 hours. Therefore, the residence time of liposomal nintedanib was much longer than that of the free drug. In addition, the liposomal drug formulations appear to be suitable for once-daily or even less frequent dosing. In comparison to free drug, liposomal nintedanib retained up to about 20-fold more nintedanib in the lung over 24 hours.

During the lung retention study, no deaths were observed for mice that were administered either a blank solution or liposomal nintedanib (Table 6). However, mice that were administered free nintedanib (as an aqueous solution) at the same 3.74 mg/mL drug concentration as the liposomal form did not fare as well. Two out of the nine mice administered free nintedanib died, with the seven surviving mice exhibiting significant weakness (Table 6). These results demonstrate that the liposomal form of nintedanib is safer and less toxic than the free form of nintedanib. These results also indicate that it would be possible to increase the nintedanib dose in the liposomal drug form above 3.74 mg/mL to enhance efficacy and prolong sustained release while still maintaining safety.

TABLE 6

Observations of mice during lung retention study

| Test Articles | Number of mice sampled at different time points (hours) | | | | Mortality |
|---|---|---|---|---|---|
|  | 0 | 2 | 6 | 24 |  |
| Blank | 3 | 0 | 0 | 0 | 0/3 |
| 3.74 mg/mL Nin (free form) | 0 | 3 | 3 | 3 | 2/9 (the 7 surviving mice were very weak) |
| 300 mM A.S. - 3.74 mg/mL Nin PEG of 0.45 mol % (liposomal form) | 0 | 3 | 3 | 3 | 0/9 |
| 300 mM A.S. - 3.74 mg/mL Nin PEG of 1.75 mol % (liposomal form) | 0 | 3 | 3 | 3 | 0/9 |

Example 7

Lung Retention of TKI in an IPF Animal Model

To expand upon the lung retention study of Example 6, retention of nintedanib in mouse lung tissue was also investigated in an IPF model. The study design details are given in Table 7. Briefly, 21 mice were divided into two groups (two different nintedanib compositions) with nine mice in Group #1 and 12 mice in Group #2.

The description of each nintedanib composition is given below:
Group #1: AS-Nin 3.74 mg/mL-PEG3% represented nintedanib loaded into 300 mM A.S. liposomes comprising 3 mol % PEG; lipid concentration of 15 mM, nintedanib concentration of 3.74 mg/mL;
Group #2: free nintedanib represented 150 mg nintedanib soft capsules (free nintedanib solutions were prepared daily by dissolving the soft capsule content in sesame oil to yield a nintedanib concentration of 7.6 mg/mL for dosing; volume for oral administration was 200 μL/mouse).

First, pulmonary fibrosis was induced by IT instillation of 2.5 mg/kg bleomycin to each mouse. After seven days, either 25 μL of liposomal nintedanib (Group #1) was instilled intratracheally or oral nintedanib (Group #2), one of two FDA-approved drugs for IPF treatment, was administered orally to the fibrotic mice. The dosing regimens are shown in Table 7. Q2D×2 signifies one dose administered every other day for a total of two doses. Blood and lung tissue samples were collected at predetermined time points (Table 7).

TABLE 7

Study design of lung retention of nintedanib in an IPF animal model

| Group # | Composition | Number of animals | Dose frequency (numbers) | Blood/lung tissue sampling time points (post-dose)* |
|---|---|---|---|---|
| 1 | AS-Nin 3.74 mg/mL-PEG3% (4.68 mg/kg, IT) | 9 | Once (N = 6) Q2D×2 (N = 3) | 24 and 48 h 48 h |
| 2 | free nintedanib (60 mg/kg, oral) | 12 | Once (N = 6) QD for 5 days (N = 6) | 1 and 5 h 1 and 5 h |

*3 mice per time point in all groups.

Figure 5:
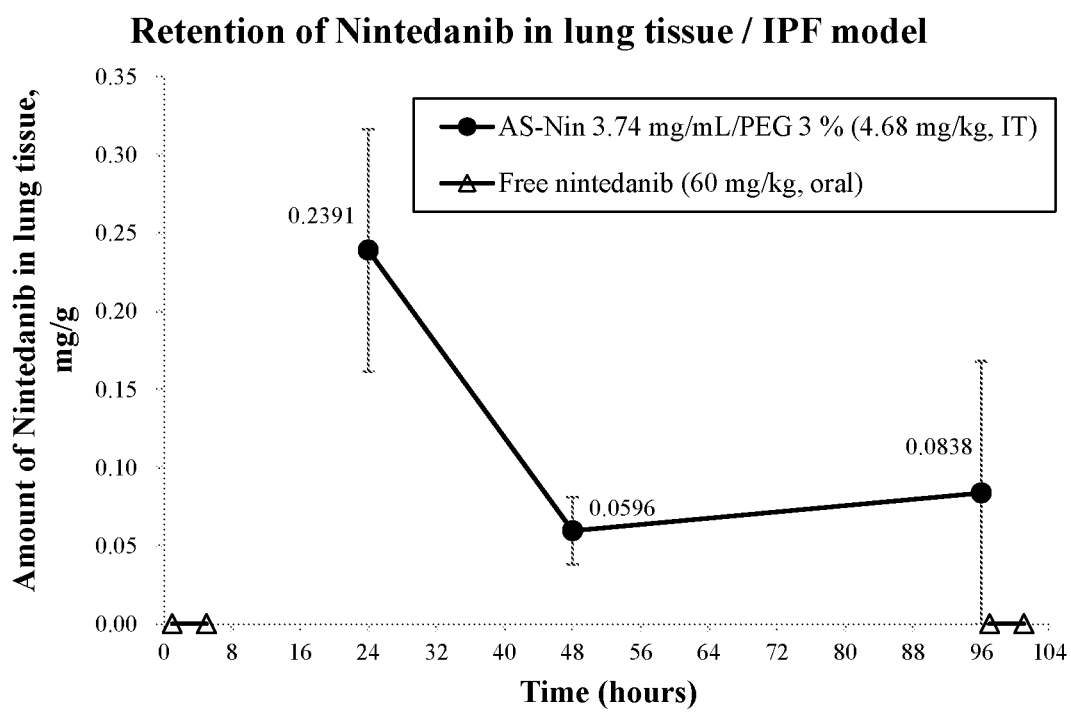
FIG. 5 is a graph depicting the retention of nintedanib (Nin) in mouse lung tissue in an IPF animal model; the figure compares the retention of nintedanib administered intratracheally (IT) in a liposomal TKI formulation comprising 300 mM AS, 3.74 mg/mL nintedanib, and 3 mol % PEG-modified lipid (closed circle) to the retention of nintedanib administered orally (free nintedanib) (open triangle); AS=ammonium sulfate; error bars represent the standard deviation.

The lung retention results from the IPF animal model study are shown in FIG. 5. The amount of nintedanib in mouse lung tissue was determined and monitored for up to five days. Despite once-daily oral dosing of 60 mg/kg nintedanib, free nintedanib showed very little, if any, drug retention in mouse lung as no nintedanib was detected in lung tissue after just a few hours. In contrast, an IT dose of 4.68 mg/kg liposomal nintedanib administered every other day yielded sustained drug release in mouse lung tissue for up to 48 hours. In addition, more than 12% of the instilled dose of the 300 mM A.S. liposomal nintedanib formulation (~0.06 mg of drug/g of lung tissue) was still observed in lung tissue after 48 hours. These results demonstrate that our liposomal drug formulation, at a significantly lower dose, was vastly superior to oral drug in prolonging retention of nintedanib in the lung of diseased mice and that infrequent dosing of inhaled liposomal nintedanib is possible.

Example 8

Efficacy of Inhaled Liposomal Nintedanib in an IPF Animal Model

The efficacy of liposomal and oral nintedanib in treating bleomycin-induced pulmonary fibrosis in mice was investigated. The study design details are given in Table 8. Briefly, eight mice were divided into three groups (N=3 each for two different nintedanib compositions and administration routes, N=2 for untreated control).

The description of each nintedanib composition is given below:

Group #1: AS-Nin 3.74 mg/mL-PEG3% represented nintedanib loaded into 300 mM A.S. liposomes comprising 3 mol % PEG; lipid concentration of 15 mM, nintedanib concentration of 3.74 mg/mL;

Group #2: free nintedanib represented 150 mg nintedanib soft capsules (free nintedanib solutions were prepared daily by dissolving the soft capsule content in sesame oil to yield a nintedanib concentration of 7.6 mg/mL for dosing; volume for oral administration was 200 μL/mouse.)

First, pulmonary fibrosis was induced by IT instillation of bleomycin at 2.5 mg/kg on day 0. After seven days, either 25 μL of liposomal nintedanib (Group #1, N=3) was instilled intratracheally or free nintedanib (Group #2, N=3) was administered orally to the fibrotic mice for the evaluation of therapeutic effect compared to untreated control (Group #3, N=2). The dosing regimens of the nintedanib compositions are shown in Table 8. Q2D×4 signifies one dose administered every other day on day 7, 9, 15, and 17. QD×10 signifies mice received once daily dosing on day 7, 8, 9, 10, 11, 14, 15, 16, 17, and 18. Blood and lung tissue samples were collected on day 21.

TABLE 8

Study design of nintedanib efficacy study in an IPF animal model

| Group # | Composition | Animal No. | Dose frequency | Blood/lung tissue sampling time points |
|---|---|---|---|---|
| 1 | AS-Nin3.74 mg/mL-PEG3% (4.68 mg/kg, IT) | 1 to 3 | Q2D×4 | Day 21 |
| 2 | free nintedanib (60 mg/kg, oral) | 4 to 6 | QD×10 | Day 21 |
| 3 | Untreated control | 7 to 8 | N/A | Day 21 |

Efficacy was determined by histopathological evaluation of mouse lung tissue. Table 9 shows the histopathological results after treatment of fibrotic mice with Groups #1-3. Reduction of lung fibrosis was observed in both Group #1 and Group #2 compared with Group #3, as lungs exhibited slight chronic, bronchioloalveolar inflammation and slight interstitial and subpleural fibrosis after treatment with either liposomal or free nintedanib (fibrosis score of ~2). Because Example 7 demonstrates that IT administration of liposomal nintedanib results in a higher concentration of drug in lung tissue for longer periods of time, our data show that intratracheal instillation of liposomal nintedanib could greatly reduce the required dose and frequency of orally administered nintedanib for the treatment of IPF.

TABLE 9

Histopathological results of mouse lung tissue in efficacy study (scored by Masson's trichrome staining)

| Histopathological findings | Group #1: liposomal nintedanib (4.68 mg/kg, IT) | | | Group #2: free nintedanib (60 mg/kg, oral) | | | Group #3: untreated control | |
|---|---|---|---|---|---|---|---|---|
| Animal No. | 1 | 2 | 3 | 4 | 5 | 6 | 7 | 8 |
| Interstitial and subpleural, multifocal fibrosis scores | 2 | 3 | 2 | 2 | 2 | 2 | 5 | 4 |
| | 2 | 2 | 2 | 2 | 2 | 2 | 4 | 3 |
| | 2 | 2 | 2 | 2 | 1 | 2 | 4 | 3 |
| | 2 | 2 | 2 | 2 | 1 | 2 | 3 | 2 |
| | 2 | 2 | 1 | 2 | 1 | 2 | 3 | 2 |
| Mean score | 2.0 | 2.2 | 1.8 | 2.0 | 1.4 | 2.0 | 3.8 | 2.8 |

Degree of lesions stained with HE was graded from one to five depending on severity: 1=minimal (<1%); 2=slight (1-25%); 3=moderate (26-50%); 4=moderate/severe (51-75%); 5=severe/high (76-100%).

REFERENCES CITED

U.S. PATENT DOCUMENTS

| | | | |
|---|---|---|---|
| 8,071,127 | B2 | December 2011 | Cipolla et al. |
| 8,119,156 | B2 | February 2012 | Cipolla et al. |
| 8,226,975 | B2 | July 2012 | Weers |
| 8,652,512 | B2 | February 2014 | Schmehl et al. |
| 8,802,137 | B2 | August 2014 | Boni et al. |
| 9,078,897 | B1 | July 2015 | Cipolla et al. |
| 9,333,214 | B2 | May 2016 | Gupta et al. |
| 9,408,836 | B2 | August 2016 | Armendáriz Borunda et al |
| 9,545,401 | B2 | January 2017 | Cipolla et al. |

FOREIGN PATENT DOCUMENTS

| | | |
|---|---|---|
| EP | 0223831 | July 1992 |
| EP | 0267050 | September 1994 |
| EP | 1438955 | June 2006 |
| EP | 1530466 | December 2014 |
| EP | 1658851 | May 2006 |
| EP | 2079443 | August 2014 |
| EP | 2363114 | May 2015 |
| EP | 2384751 | September 2015 |
| WO | WO 2015/106150 | November 2016 |
| WO | WO 2016/178064 | November 2016 |

OTHER PUBLICATIONS

K. D. Kistler, L. Nalysnyk, P. Rotella, D. Esser. Lung transplantation in idiopathic pulmonary fibrosis: a systematic review of the literature. *BMC Pulmonary Medicine.* 14: 139 (2014).

L. Nalysnyk, J. Cid-Ruzafa, P. Rotella, D. Esser. Incidence and prevalence of idiopathic pulmonary fibrosis: review of the literature. *Eur Respir Rev.* 21(126): 355-361 (2012).

European Medicines Agency, Committee for Medicinal Products, Ofev: EPAR—Public assessment report, EMA/76777/2015, Procedure No. EMEA/H/C/003821/0000, 20 Nov. 2014.

L. Richeldi et al. Efficacy and safety of nintedanib in idiopathic pulmonary fibrosis. *N Engl J Med* 370(22): 2071-2082 (2014).

T. Corte et al. Safety, tolerability and appropriate use of nintedanib in idiopathic pulmonary fibrosis. *Respiratory Research* 16: 116 (2015).

Center for Drug Evaluation and Research, Clinical Pharmacology Review, NDA #205832, 505(b)(1) priority review.
http://www.rxlist.com/ofev-side-effects-drug-center.htm
https://www.rxlist.com/esbriet-drug.htm
https://www.healthandlife.com.tw/index.php?action=products_data&id=142&width=1280

L. Wollin, E. Wex, A. Pautsch, G. Schnapp, K. E. Hostettler, S. Stowasser, M. Kolb. Mode of action of nintedanib in the treatment of idiopathic pulmonary fibrosis. *Eur Respir J.* 1-12 (2015).

J. S. Patton, P. R. Byron. Inhaling medicines: delivering drugs to the body through the lungs. *Nature Reviews Drug Discovery.* 6: 67-74 (2007).

D. Zucker, D. Marcus, Y. Barenholz, A. Goldblum. Liposome drugs' loading efficiency: A working model based on loading conditions and drug's physicochemical properties. *Journal of Controlled Release.* 139: 73-80 (2009).

O. O. Okusanya et al. Pharmacokinetic and pharmacodynamic evaluation of liposomal amikacin for inhalation in cystic fibrosis patients with chronic pseudomonal infection. *Antimicrobial Agents and Chemotherapy.* 53(9): 3847-3854 (2009).

J. P. Clancy et al. Phase II studies of nebulised Arikace in CF patients with *Pseudomonas aeruginosa* infection. *Thorax.* 68: 818-825 (2013).

D. Cipolla, J. Blanchard, I. Gonda. Development of liposomal ciprofloxacin to treat lung infections. *Pharmaceutics.* 8: 6 (2016).

C.S. Schneider et al. Nanoparticles that do not adhere to mucus provide uniform and long-lasting drug delivery to airways following inhalation. *Sci. Adv.* 3, e1601556 (2017).

S. Anabousi et al. Effect of PEGylation on the stability of liposomes during nebulization and in lung surfactant. *Journal of Nanoscience and Nanotechnology.* 6: 3010-3016 (2006).

P. Muralidharan, E. Mallory, M. Malapit, D. Hayes Jr, H. M. Mansour. Inhalable PEGylated phospholipid nanocarriers and PEGylated therapeutics for respiratory delivery as aerosolized colloidal dispersions and dry powder inhalers. *Pharmaceutics.* 6: 333-353 (2014).

F. J. Bayard, W. Thielemans, D. I. Pritchard, S. W. Paine, S. S. Young, P. Backman et al. Polyethylene glycol-drug ester conjugates for prolonged retention of small inhaled drugs in the lung. *J Control Release: Off J Control Release Soc.* 171: 234-240 (2013).

T. W. Shen et al. Distribution and cellular uptake of PEGylated polymeric particles in the lung towards cell-specific targeted delivery. *Pharm Res.* 32(10): 3248-3260 (2015).

Y. S. Youn, M. J. Kwon, D. H. Na, S. Y. Chae, S. Lee, K. C. Lee. Improved intrapulmonary delivery of site-specific PEGylated salmon calcitonin: optimization by PEG size selection. *J Control Release: Off J Control Release Soc.* 125: 68-75 (2008).

G. Rouser, S. Fkeischer, A. Yamamoto. Two dimensional thin layer chromatographic separation of polar lipids and determination of phospholipids by phosphorus analysis of spots. *Lipids* 5: 494-496 (1970).

What is claimed is:

1. A liposomal sustained-release composition for use in the treatment of a pulmonary disease via inhalation, comprising liposomes having entrapped nintedanib, wherein each liposome comprises:
    a lipid bilayer comprising one or more phospholipids, a sterol, and a polyethylene glycol (PEG)-modified lipid; and
    an aqueous interior encompassed by the lipid bilayer and entrapping the nintedanib;
    wherein the liposomes have a mean particle diameter between about 50 nm and about 400 nm; and
    wherein the composition has a ratio of nintedanib-to-phospholipid from about 0.1 mol nintedanib/mol phospholipid to about 2.5 mol nintedanib/mol phospholipid.

2. The liposomal sustained release composition of claim 1, wherein the composition has a nintedanib-to-phospholipid ratio selected from a range of about 100 g nintedanib/mol phospholipid to about 1,000 g nintedanib/mol phospholipid, and about 200 g nintedanib/mol phospholipid to about 1000 g nintedanib/mol phospholipid.

3. The liposomal sustained release composition of claim 1, wherein the composition has a lipid concentration ranging from about 1 mM to about 25 mM.

4. The liposomal sustained release composition of claim 1, wherein the concentration of the nintedanib ranges from about 1 mg/mL to about 15 mg/mL.

5. The liposomal sustained release composition of claim 4, wherein the PEG-modified lipid is present in an amount less than 6 mol % on the basis of the total phospholipids and sterol.

6. The liposomal sustained release composition of claim 1, wherein the pulmonary disease is selected from the group consisting of pulmonary fibrosis, non-small cell lung cancer, and systemic sclerosis.

7. The liposomal sustained release composition of claim 1, wherein the PEG-modified lipid has a PEG moiety with an average molecular weight ranging from about 1,000 g/mol to about 5,000 g/mol.

8. The liposomal sustained release composition of claim 7, wherein the PEG-modified lipid is 1,2-distearoyl-sn-glycero-3-phosphoethanolamine-N-[methoxy(polyethylene glycol)] (DSPE-PEG).

9. The liposomal sustained release composition of claim 8, wherein the one or more phospholipids is a neutral phospholipid and the DSPE-PEG of the liposome is present in an amount ranging from about 0.001 mol % to about 5 mol % on the basis of total phospholipid and sterol.

10. The liposomal sustained release composition of claim 1, wherein the one or more phospholipids is selected from the group consisting of hydrogenated soy phosphatidylcholine (HSPC), 1,2-distearoyl-sn-glycero-3-phosphocholine (DSPC), 1,2-dipalmitoyl-sn-glycero-3-phosphocholine (DPPC), phosphatidylethanolamine lipid, and combinations thereof.

11. The liposomal sustained release composition of claim 1, wherein the molar ratio of the total phospholipids to sterol ranges from about 1:1 to about 3:2.

12. The liposomal sustained release composition of claim 1, wherein the nintedanib is encapsulated in the aqueous interior of the liposome via a transmembrane pH gradient-driven remote loading method using a trapping agent.

13. The liposomal sustained release composition of claim 12, wherein the trapping agent is ammonium sulfate.

14. An aerosolized composition of particles for use in the treatment of a pulmonary disease, comprising the liposomal sustained release composition of claim 1.

15. The aerosolized composition of particles of claim 14, wherein the particles have a mass median aerodynamic diameter of from about 0.5 μm to about 5 μm.

16. The aerosolized composition of particles of claim 14, wherein the liposomes with the entrapped nintedanib have a release rate between about 0.5% and about 25% of total nintedanib per hour in the lung with complete release of the entrapped nintedanib occurring after a minimum of about 12 hours or a minimum of about 24 hours.

17. The aerosolized composition of particles of claim 14, which is administered at an amount of 0.001 mg/kg to 50 mg/kg.

* * * * *